United States Patent
Holländer et al.

(10) Patent No.: US 10,273,470 B2
(45) Date of Patent: Apr. 30, 2019

(54) METHOD FOR ISOLATING RNA FROM A RNA AND DNA CONTAINING SAMPLE

(75) Inventors: Vera Holländer, Unna (DE); Gabriele Christoffel, Köln (DE)

(73) Assignee: QIAGEN GmbH, Hilden (DE)

( * ) Notice: Subject to any disclaimer, the term of this patent is extended or adjusted under 35 U.S.C. 154(b) by 0 days.

(21) Appl. No.: 13/580,470

(22) PCT Filed: Feb. 25, 2011

(86) PCT No.: PCT/EP2011/000930
§ 371 (c)(1),
(2), (4) Date: Nov. 6, 2012

(87) PCT Pub. No.: WO2011/104032
PCT Pub. Date: Sep. 1, 2011

(65) Prior Publication Data
US 2013/0052721 A1    Feb. 28, 2013

(30) Foreign Application Priority Data

Feb. 26, 2010 (EP) .................................... 10001995
Mar. 3, 2010 (EP) .................................... 10002171

(51) Int. Cl.
*C12N 15/00* (2006.01)
*C12N 15/10* (2006.01)

(52) U.S. Cl.
CPC ................................ *C12N 15/1003* (2013.01)

(58) Field of Classification Search
CPC ......... A01N 1/0231; C12N 1/063; G01N 1/30
USPC ............................. 435/283.1, 379, 40.5, 6.11
IPC .............. C07H 21/00; C12N 5/02; G01N 1/30
See application file for complete search history.

(56) References Cited

U.S. PATENT DOCUMENTS

| | | | |
|---|---|---|---|
| 6,218,531 B1 | 4/2001 | Ekenberg | |
| 7,964,350 B1* | 6/2011 | Fekete ............... | C12N 15/1003 435/6.12 |
| 9,200,313 B2* | 12/2015 | Bengtsson ........... | C12Q 1/6806 |
| 2005/0042660 A1 | 2/2005 | Hall, Jr. et al. | |
| 2007/0082354 A1 | 4/2007 | Leiser et al. | |
| 2009/0136971 A1 | 5/2009 | Krizman et al. | |

FOREIGN PATENT DOCUMENTS

| | | |
|---|---|---|
| DE | 10 2005 060 738 A1 | 6/2007 |
| DE | 10 2008 029 356 A1 | 12/2009 |
| DE | 10 2008 061 714 A1 | 6/2010 |
| EP | 1 526 176 A2 | 4/2005 |
| EP | 1 767 631 A1 | 3/2007 |
| EP | 2 163 622 A1 | 3/2010 |
| WO | 01/46402 A1 | 6/2001 |
| WO | 03/064605 A2 | 8/2003 |
| WO | 2005/012523 A1 | 2/2005 |
| WO | 2005/054466 A2 | 6/2005 |
| WO | 2005/075642 A1 | 8/2005 |
| WO | 2006/083962 A1 | 8/2006 |
| WO | 2007/068764 A1 | 6/2007 |
| WO | 2008/021419 A2 | 2/2008 |
| WO | 2009/144182 A1 | 12/2009 |

OTHER PUBLICATIONS

Qiagen Proteinase K product data sheet (accessed May 3, 2014).*
Detergent—definition of detergent by The Free Dictionary, http://www.thefreedictionary.com/detergent.*
Qiagen (2003. RNeasy® MinElute™ Cleanup Handbook for RNA cleanup and concentration with small elution volumes, 32 Pages.*
Schultes et al. 1997. Global similarities in nucleotide base composition among disparate functional classes of single-stranded RNA imply adaptive evolutionary convergence. RNA, vol. 3: pp. 792-806.*
Ribeiro-Silva et al. 2007. RNA extraction from ten year old formalin-fixed paraffin-embedded breast cancer samples: a comparison of column purification and magnetic bead-based technologies. BMC Molecular Biology, vol. 8, pp. 118-1-10.*
Jahn (i.e., Jahn et al. 2008. Evaluation of isolation methods and RNA integrity for bacterial RNA quantitation. Journal of Microbiological Methods, vol. 75, pp. 318-324 (Year: 2008).*
Detergent—definition of detergent by The Free Dictionary, http://www.thefreedictionary.com/detergent, accessed Jun. 15, 2015.*
International Search Report and Written Opinion, dated May 27, 2011, for PCT/EP2011/000920, 10 pages.
International Search Report and Written Opinion, dated May 27, 2011, for PCT/EP2011/000930, 9 pages.
Genov et al., "Stability of subtilisins and related proteinases (subtilases)," *Int J Peptide Protein Res* 45:391-400, 1995.
miRNeasy FFPE Handbook, QIAGEN, Sep. 2010, 41 pages.
O'Shea et al., "Analysis of T receptor β chain CDR3 size using RNA extracted from formalin fixed paraffin wax embedded tissue," *J Clin Pathol* 50:811-814, 1997.
RNeasy FFPE Handbook, QIAGEN, Sep. 2010, 41 pages.
"Protein Purification Extraction and Clarification," European Molecular Biology Laboratory, Feb. 1, 2002, retrieved from URL=http://www.embl.de/pepcore/pepcore_services/protein_purification/extraction_clarification/lysis_buffer_additives, on Jul. 25, 2013, 2 pages.
RNeasy® FFPE Handbook, Qiagen, Jan. 2006, 28 pages.
Kristensen et al., "Quality assessment of DNA derived from up to 30 years old formalin fixed paraffin embedded (FFPE) tissue for PCR-based methylation analysis using SMART-MSP and MS-HRM," *BMC Cancer* 9:453, 2009, 11 pages.
Tucker et al., "Massively Parallel Sequencing: The Next Big Thing in Genetic Medicine," *The American Journal of Human Genetics* 85:142-154, Aug. 14, 2009.
RNeasy® Mini Handbook, QIAGEN, Third Edition (116 pages) (Jun. 2001).

* cited by examiner

*Primary Examiner* — Aaron A Priest
(74) *Attorney, Agent, or Firm* — Seed IP Law Group LLP

(57) ABSTRACT

The present invention pertains to a method for isolating RNA, including small RNA from a RNA and DNA containing sample, wherein the sample is lysed and the optionally further processed lysate is incubated with a DNase to degrade DNA prior to purifying the RNA from the optionally further processed lysate. It was found that performing the DNase digest prior to isolating the RNA from the lysate has considerable advantages.

24 Claims, 1 Drawing Sheet

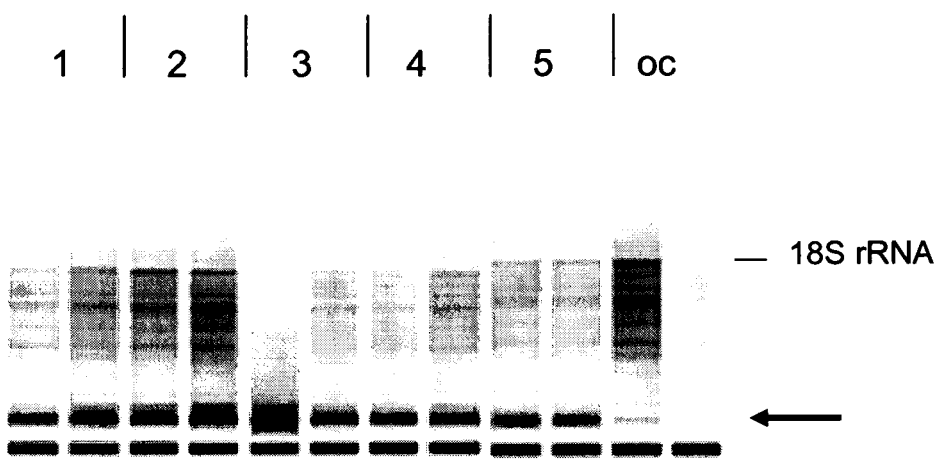

METHOD FOR ISOLATING RNA FROM A RNA AND DNA CONTAINING SAMPLE

The present invention pertains to methods for isolating RNA from a RNA and DNA containing sample, and in particular provides means for efficiently isolating RNA with a reduced amount of DNA contaminations from a respective sample. Furthermore, the present invention allows to isolate RNA including small RNA with good yield if desired.

The study of small nucleic acids in the order of 1000 or 500 nucleotides or less from various samples such tissues, blood, body fluids and organisms is an area of extreme interest and promises to remain one for the future. Small nucleic acids in particular include small RNAs such as inter alia micro RNAs (miRNA) and small interfering RNA molecules both of which can have a powerful effect on the expression of a gene. Furthermore, also other small nuclear and small nucleolar RNAs (e.g. snRNAs and snoRNAs) involved in mRNA and rRNA processing are of interest. Furthermore, RNA having a length of 1000 or 500 nucleotides or less are also often contained as degradation products in special samples such as cross-linked samples, e.g. samples that have been formalin fixed and paraffin-embedded (FFPE samples), because the respective preservation may compromise the RNA integrity.

With the increasing interest in respective small RNAs, the standard isolation procedures have been modified to facilitate the isolation of small RNAs and in particular to improve the yield of small RNAs. This is, because the known protocols used as standard to isolate RNA are usually not ideal for isolating small RNA because the small RNA is often not effectively captured and eluted during the isolation process using the standard methods. Therefore, the RNA isolated from samples using standard procedures usually do not comprise the small RNA in sufficient amounts and thus do not provide acceptable yields because the small RNA is either not bound or gets lost during the nucleic acid isolation procedure. Thus, there is a need for improved techniques for the efficient isolation of small RNA either alone or as a portion of the isolated total RNA.

Methods that have been optimized for the isolation of small nucleic acids often rely on phenol and chloroform extraction and stepwise alcohol fractionation. According to one embodiment, the RNA is concentrated in the aqueous phase and is then subsequently isolated therefrom e.g. by adding at least one alcohol and binding the RNA to a membrane. Here, it is also important to efficiently capture the small RNAs in the isolated total RNA.

Furthermore, methods for isolating RNA including small RNA have been developed which involve the use of chaotropic agents, high concentrations of alcohol and nucleic acid binding columns which comprise e.g. a nucleic acid binding membrane such as a silica membrane. Total RNA isolated with these protocols comprises small RNAs, if respective small RNAs are contained in the sample. Respective membrane-based isolation protocols are in particular suitable for isolating small nucleic acids either alone or as a portion of the total target nucleic acid from various samples.

A further issue when isolating RNA is the purity of the obtained RNA. The aim is to obtain the RNA with high purity, i.e. contaminants such as proteins or DNA shall be efficiently removed. For many applications of the purified RNA, DNA contaminations pose a problem. Therefore, several measures were developed in the prior art for reducing the amount of DNA contaminations in the isolated RNA. According to one method, the DNA comprised in the sample is first selectively bound to a solid phase and is removed together with the solid phase thereby depleting the sample of DNA. Other methods involve the use of a DNase to digest DNA contaminations. In RNA purification methods, DNase digests are usually performed either on the eluted RNA or, if using a nucleic acid binding solid phase comprised in a column, a so called on-column DNase digest is performed. Here, the RNA is first bound to the column, optionally washed and the DNase and an appropriate reaction buffer is applied to the column and the DNase digest is being performed while the RNA is bound to the column. However, both methods have draw-backs. Performing a DNase digest on the eluted RNA has the effect that the DNase and thus an undesired protein contamination is comprised in the purified RNA. Furthermore, the DNase must be inactivated for certain downstream applications of the purified RNA e.g. when transcribing the RNA to cDNA. Thus, often an additional purification (cleanup) step is performed, to remove the DNase from the eluate. This increases hands on time and furthermore, poses the risk that the RNA yield is reduced due to the clean-up. Performing an on-column DNase digest has the drawback that it decreases the yield of RNA and in particular the yield of small RNA because the DNase digest has the effect that at least a portion of the bound RNA and in particular the small RNA is released from the nucleic acid binding solid phase during said on-column treatment.

Thus, it is inter alia the object of the present invention to provide a method for isolating RNA which provides pure RNA comprising little or even no DNA contaminations. Furthermore, it is an object to increase the yield of small RNA in the isolated RNA. Furthermore, it is an object to provide a method that is well suitable for automation.

SUMMARY OF THE INVENTION

The present invention is based on the finding that a method for isolating RNA from a RNA and DNA containing sample can be improved if a DNase digest is performed after the sample was degraded, e.g. lysed, but before the RNA is isolated from the degraded sample e.g. by binding the RNA to a nucleic acid binding solid phase. Thus, in contrast to the prior art which performs the DNase digest after the RNA has been isolated from the lysate (e.g. by binding RNA to a solid phase and performing a DNase digest while the nucleic acid is bound to said solid phase or by performing a DNase digest on the purified, eluted RNA), the present invention teaches to perform the DNase digest before the RNA is isolated from the degraded sample. It was surprisingly found that performing a DNase digest prior to isolating the RNA has important advantages, because in particular the yield of small RNAs in the isolated RNA can be increased compared to prior art methods, in particular compared to the common on-column DNase digest. Additionally, performing a DNAse digest on the degraded sample is with respect to the handling simpler as an on-column DNase treatment. Thus, the method according to the present invention wherein the DNase digest is performed before isolating the RNA is easily suitable for automation, while automation is more cumbersome when using an RNA purification method which involves an on-column DNase digest. Furthermore, in contrast to prior art methods wherein the DNase digest is performed on the RNA eluate, the method according to the present invention avoids a contamination of the purified RNA with DNase. Moreover, the method according to the present invention can be advantageously used for several different sample types.

According to a first aspect, a method for isolating RNA, in particular RNA comprising small RNA, from a RNA and DNA containing sample is provided, said method comprising at least the following steps
 a) degrading the sample;
 b) optionally separating undissolved constituents from the degraded sample;
 c) incubating at least a portion of the degraded, optionally further processed sample with a DNase; and
 d) isolating the RNA from the DNase treated sample.

According to a further aspect, a method for isolating RNA, including small RNA from a RNA and DNA containing sample is provided, wherein the sample is lysed and at least a portion of the optionally further processed lysate is incubated with a DNase to degrade DNA prior to purifying the RNA from the optionally further processed lysate.

Other objects, features, advantages and aspects of the present application will become apparent to those skilled in the art from the following description and appended claims. It should be understood, however, that the following description, appended claims, and specific examples, while indicating preferred embodiments of the application, are given by way of illustration only. Various changes and modifications within the spirit and scope of the disclosed invention will become readily apparent to those skilled in the art from reading the following.

BRIEF DESCRIPTION OF THE FIGURES

FIG. 1: Agilent Bioanalyzer analysis of isolated RNA. 1-5: Samples with DNAse pretreatment using pretreatment buffer 1-5 as described in example 1. oc: Samples without DNAse pretreatment, but with on column DNAse treatment as it is common in the prior art.

DETAILED DESCRIPTION OF THE INVENTION

As discussed above, it was surprisingly found that performing a DNase digest prior to isolating the RNA from the degraded sample has important advantages over prior art methods, in particular with respect to the possible yield of small RNAs, the purity and the handling of the samples.

Therefore, a method for isolating RNA from a RNA and DNA containing sample is provided, said method comprising at least the following steps
 a) degrading the sample;
 b) optionally separating undissolved constituents from the degraded sample;
 c) incubating at least a portion of the degraded, optionally further processed sample with a DNase; and
 d) isolating the RNA from the DNase treated sample.

Said method is in particular suitable for isolating RNA including small RNA from a RNA and DNA containing sample.

The degradation of the sample performed in step a) in particular results in a denaturing and/or lysis of the sample. The terms "degradation" and "lysis" as used herein intend to describe not only a step which releases cells from tissue and/or breaks open cells but also refers to a step wherein e.g. a cell-free sample or a sample wherein the cells were already opened to release the nucleic acids is degraded, and in particular refers to a step wherein said degradation assist the release the nucleic acids from complexing sample constituents, e.g. proteins, and/or a step which digests or denatures proteins or other sample constituents which could interfere with the subsequent purification. If using the term "a" in conjunction with a certain additive or component, it usually means "at least one" unless a different meaning is evident from the context.

According to one embodiment, the sample degradation in step a) is performed in the presence of at least one degrading additive selected from the group consisting of proteolytic enzymes, detergents, chaotropic agents, organic solvents and alkaline agents. Sample degradation in step a) may also be achieved or supported by mechanical degradation, homogenisation and/or heating of the sample. Further additives can be used in degradation step a) that can support the lysis of the sample, the degradation of proteins and/or which preserve the RNA during degradation or which preserve the RNA in the degraded sample. Examples include, but are not limited to
 complex formers, preferably ethylenediamine-N,N,N',N'-tetraacetic acid (EDTA), ethylene glycol bis(2-aminoethyl ether)-N,N,N',N'-tetraacetic acid (EGTA) sodium citrate or mixtures of these,
 reducing agents, preferably selected from the group comprising dithiothreitol (DTT), dithioerythritol (DTE), sodium thiosulfate, β-mercaptoethanol or mixtures of these,
 inorganic salts, preferably alkali metal halides, particularly preferably NaCl, KCl or LiCl, alkaline earth metal halides, particularly preferably $CaCl_2$ or $MgCl_2$, ammonium salts, particularly preferably ammonium chloride or ammonium sulphate, lithium sulphate or mixtures of these,
 buffering agents such as Tris, HEPES, Pipes, MES, MOPS, sodium citrate, sodium acetate, BIS-TRIS Propane, alkali metal acetate/acetic acid,
 stabilising agents,
 nuclease inhibitors, in particular ribonuclease inhibitors, and
 further enzymes such as hydrolases and lipases.

According to one embodiment, the sample is degraded in step a) by adding at least one proteolytic enzyme. Preferably, degradation is assisted by additionally using at least one detergent and/or at least one chaotropic agent.

According to one embodiment, the sample is degraded in step a) by adding at least one detergent. Preferably, degradation is assisted by additionally using a proteolytic enzyme.

When using at least one proteolytic enzyme in step a), incubation conditions are used that ensure that said enzyme works efficiently and is catalytically active. The conditions depend on the proteolytic enzyme used and are known, respectively determinable by the skilled person. Preferably, the incubation in step a) for degrading the sample is performed in the presence of salts and/or ions that promote and/or maintain the activity of the proteolytic enzyme. Suitable salts include but are not limited to NaCl, KCl, $MgCl_2$, or $CaCl_2$ or chaotropic agents such as chaotropic salts. Preferably, the incubation with at least one proteolytic enzyme is performed at a pH between 4 to 9, 6 to 8 and, preferably, is performed at a neutral pH value. The optimal pH depends on chosen enzyme. In order to ensure efficient degradation of proteins, the sample should be incubated in step a) for a period of at least 5 minutes, at least 10 minutes and preferably at least 15 min in order to ensure efficient protein degradation by the proteolytic enzyme. Depending on the sample type to be degraded, also considerably larger incubation periods can be advantageous to ensure that the RNA (and potentially the DNA) is efficiently released. According to one embodiment involving a proteolytic enzyme in step a), the incubation is performed in step a) for a period of 1 min to 48 h, 5 min to 24 h, 10 min to 12 h, 10 min to 5 h, 10 min to 3 h, 5 min to 100 min or preferably 5 min to 90 min. The incubation time depends on the chosen degradation conditions, the sample type and the purpose of the degradation which can, e.g., be advantageously used, if desired, in conjunction with cross-linked samples to selectively release RNA from the sample while keeping the DNA predominantly in the undegraded, undissolved fraction of the sample. This particular embodiment will be explained in further detail below.

When using a proteolytic enzyme, the degradation in step a) is preferably performed under heating and thus elevated temperatures. The heating temperature is chosen such that the proteolytic enzyme is active and preferably lies in a range of 30 to 80° C., preferably 40 to 65° C. The degradation with the proteolytic enzyme can be supported by agitation.

A proteolytic enzyme refers to an enzyme that catalyzes the cleavage of peptide bounds, for example in proteins, polypeptides, oligopeptides and peptides. Exemplary proteolytic enzymes include but are not limited to proteinases and proteases in particular subtilisins, subtilases, alkaline serine proteases and the like. Subtilases are a family of serine proteases, i.e. enzymes with a serine residue in the active side. Subtilisins are bacterial serine proteases that have broad substrate specificities. Subtilisins are relatively resistant to denaturation by chaotropic agents, such as urea and guanidine hydrochloride and anionic detergents such as sodium dodecyl sulfate (SDS). Exemplary subtilisins include but are not limited to proteinase K, proteinase R, proteinase T, subtilisin, subtilisin A, QIAGEN Protease and the like. Discussions of subtilases, subtilisins, proteinase K and other proteases may be found, among other places in Genov et al., Int. J. Peptide Protein Res. 45: 391-400, 1995. Preferred are proteases and heat-stable proteases, particularly preferably proteinase K, trypsin, chymotrypsin, papain, pepsin, pronase and endoproteinase Lys-C. Preferably, the proteolytic enzyme is proteinase K. Using a proteolytic enzyme such as proteinase K has the advantage that the proteolytic enzyme also digests itself during the incubation. The incubation using the proteolytic enzyme is performed under conditions wherein the proteolytic enzyme is active. Suitable conditions which work particularly well for proteases such as proteinase K are described above.

In non-limiting aspects, the proteolytic enzyme is used in degradation step a) in a concentration between about 0.001 mg/ml to about 100 mg/ml. In certain embodiments the range can be from about 0.01 mg/ml to about 50 mg/ml, from about 0.2 mg/ml to about 10.0 mg/ml, from about 0.2 mg/ml to about 5.0 mg/ml or from about 0.2 mg/ml to about 1.0 mg/ml. Suitable concentration ranges are also known in the prior art for different sample types and different proteolytic enzymes and can also be determined by the skilled person. Thus, they need no further description here.

Suitable detergents that can be used in degradation step a) include anionic, cationic, zwitterionic and non-ionic detergents. Anionic surfactants include but are not limited to SDS or lauryl sarkosine. Cationic detergents include but are not limited to quarternary amines or tertiary amines and include but are not limited to CTAB, DTAB and TTAB. Zwitterionic detergents include but are not limited to CHAPS and CHAPSO. Non-ionic surfactants include but are not limited to alkyl glucosides, in particular polysorbates such as polysorbate 20 (Tween 20), polysorbate 40 (Tween 40) and polysorbate 80 (Tween 80) and polyoxyethylen alkyl ethers such as Triton X-100, Nonidet P40, NP-40 and respective non-ionic detergents from the Brij class. Further detergents that are useful for lysis, respectively degradation of a sample in a method for purifying nucleic acids such as RNA are also well-known in the prior art and thus, need no detailed description here. Also a mixture of detergents can be used.

According to one embodiment, degradation is performed in step a) by adding an aqueous solution to the sample, wherein said solution comprises at least one detergent, preferably a non-ionic detergent such as SDS, and preferably at least one buffering agent, preferably TRIS. The aqueous solution may also comprise at least one chelating agent such as EDTA. Optionally but preferably, degradation is assisted by using at least one proteolytic enzyme. The proteolytic enzyme can be comprised in the aqueous solution or can be added separately. Preferably, a protease such as proteinase K is used as proteolytic enzyme.

A suitable chaotropic agent that can be used in degradation step a) to denature the sample includes but is not limited to a chaotropic salt such as a guanidinium salt, e.g. guanidinium hydrochloride, guanidinium thiocyanate, guanidinium isothiocyanate, sodium thiocyanate, sodium iodide, sodium perchlorate, sodium trichloroacetate, sodium trifluoroacetate and urea. In particular, guanidinium hydrochloride and/or guanidinium thiocyanate can be used as chaotropic agent. Respective chaotropic agents are very suitable to degrade a sample and to denature e.g. proteins and other sample components. Furthermore, chaotropic agents also act as ribonuclease inhibitors. The concentration of the at least one chaotropic agent in the degradation mixture comprising the sample and the additives used for degradation may lie in a range of 0.05M up to the saturation limit. Preferred concentration ranges lie, depending on the chaotropic agent used, in the range of about 0.1M to 10M, about 0.5M to 5M, about 1M to 3M and preferably lie in the range of about 1M to 3M. Respective concentrations can be used e.g. when using a chaotropic agent in combination with a proteolytic enzyme and/or a detergent.

According to one embodiment, degradation in step a) is achieved by using at least one chaotropic agent (suitable examples and concentration ranges are described above) and optionally, but preferably, at least one detergent. Preferably, the chaotropic agent and if present the detergent are provided in form of an aqueous solution. Said solution may also comprise further additives such as e.g. a buffer and/or a sulfhydryl reducing agent. Suitable lysis reagents containing a chaotropic agent that can be used for that purpose are described in WO 2009/144182, herein incorporated by reference. Degradation using a respective lysis solution can be supported by using a proteolytic enzyme, suitable examples and conditions are described above.

Suitable organic solvents that can be used to degrade the sample include but are not limited to alcohols, such as branched or unbranched C1 to C5 alcohols and phenol or phenol derivatives.

According to one embodiment, an acidic denaturing composition is used in step a) which comprises a chaotropic agent and phenol. Suitable chaotropic agents were described above. The chaotropic agent can be comprised in the acidic denaturing composition in a concentration selected from the group consisting of 0.1 up to the saturation limit, 0.1 to 6M, 0.5 to 4M, 0.5 to 3M and 0.5 to 2M. Phenol is preferably comprised in the acidic denaturing composition in a concentration selected from the group consisting of 10% v/v to 70% v/v, 20% v/v to 60% v/v and 30% v/v to 50% v/v based on the total volume of the acidic denaturing composition. Preferably, the concentration of phenol lies in the range of 35% v/v to 40% v/v. The pH value of the denaturing composition is acidic and may be ≤6, preferably ≤5. Preferably, the pH value of the acidic denaturing composition lies in the range of 3 and 6, and more preferred, in a range of 4 to 5. Furthermore, the acidic denaturing composition may comprise a buffer in an amount sufficient to maintain said composition at an acidic pH. Said buffer may be a salt of at least one of acetate, citrate, phosphate, phthalate, tartrate or lactate and can be e.g. selected from sodium phosphate, sodium acetate and sodium citrate. Preferably, sodium acetate is used. The acidic denaturing composition may comprise a solubilizer for maintaining the phenol in solution, especially at 4° C., and to achieve or maintain the solvent as a monophase solution. A suitable solubilizer is glycerol. According to one embodiment, the solubilizer is comprised in a concentration of about 2 to 10%, preferably about 5%. The acidic denaturing composition may comprise a solubilizer for maintaining the phenol in solution, especially at 4° C., and to achieve or maintain the solvent as a monophase solution. A suitable solubilizer is glycerol. According to one embodiment, the solubilizer is comprised in a concentration of about 2 to 10%, preferably about 5%. Furthermore, the acidic denaturing composition may comprise a thiocyanate component, preferably ammonium thiocyanate or sodium thiocyanate. This additional thiocyanate component is believed to enhance the extraction of RNA from the biological sample. The thiocyanate component may be comprised in a concentration of 0.1 to 1M, preferably 0.4M. According to one embodiment, the acidic denaturing composition that can be used in degradation step a) comprises phenol in a concentration above 30%, preferably above 35% and most preferred between 35% and 40%; comprises a chaotropic salt in a concentration of 0.5 to 4M, preferably 0.5 to 3M; has a pH of 4.3 to 6, preferably 4.5 to 5; and preferably comprises at least one further agent selected from the group consisting of a buffer, a solubilizer and a thiocyanate compound.

As discussed above, also other degradation/lysis methods can be used to degrade and thus prepare the RNA and DNA containing sample in step a).

In step b), undissolved constituents are optionally separated from the degraded sample. A respective separation step is in particular advantageous if a sample is processed which comprises cell debris or other larger components that could disturb the subsequent DNase digestion in step c) or the RNA isolation in step d). Furthermore, when processing a cross-linked sample, this separation step b) can be advantageously used in order to remove a large portion of the comprised DNA together with the undissolved constituents. This embodiment will be explained in further detail below. Additional or alternative steps can also be performed e.g. to selectively remove at least a portion of the DNA from the degraded sample prior to performing the DNase digest in step c). Such steps include, but are not limited to selectively binding the released DNA to a nucleic acid binding solid phase to remove mainly the DNA, but not the RNA, from the degraded sample. Still remaining DNA can then be efficiently digested in step c) prior to isolating the RNA from the degraded sample. However, when using the method according to the present invention, a respective intermediate step to deplete the degraded sample from DNA is only optional and not necessary, because DNA can be efficiently removed by performing the DNase digest according to step c). Thus, according to one embodiment, no intermediate step for selectively removing DNA, in particular by selectively binding the DNA to a nucleic acid solid phase, is performed prior to performing the DNase digest in step c).

In step c), a DNase digest is performed on the degraded sample (e.g. the lysate). Thus, DNase is added to the degraded sample. In contrast to the prior art, the DNase digest is according to the present invention performed prior to isolating the RNA. It was very surprising that the DNase digest can be performed efficiently on the degraded sample prior to isolating the RNA. This, as it was assumed that the DNase could not function efficiently on the degraded sample as the common prior art methods all isolate the RNA prior to performing the DNase digest when purifying RNA. Furthermore, performing the DNase digest prior to isolating the RNA also has considerably advantages because e.g. compared to the common on-column DNase treatment, the amount of in particular small RNA can be increased when using the method according to the present invention and said method is also well suitable for automation.

The term "DNase" refers to any enzyme that catalyses the hydrolytic cleavage of phosphodiester linkages in the DNA. A wide variety of deoxyribonucleases are known, which differ in their substrate specificities, chemical mechanisms, and biological functions. The term "DNase" refers to exodeoxyribonucleases as well as endodeoxyribonucleases. In particular, DNase I and DNase II can be used. DNase I is preferred.

The DNase digest in step c) is performed under conditions wherein the DNase is active to allow an efficient degradation of the DNA. The efficiency of the DNase digest can be e.g. controlled by the amount of DNase added to the degraded sample and furthermore, by the addition of additives which promote the activity of the DNase such as in particular Mg and Ca ions. Furthermore, depending on the used method for achieving degradation in step a), intermediate processing steps might be advantageous to ensure that the DNase digest works with high efficiency on the degraded sample. E.g. when using an organic solvent such as phenol for degradation, it is recommended to remove the phenol containing phase prior to subjecting the aqueous phase comprising the lysed sample to the DNase digest in step c). The aqueous phase can also be diluted to further reduce the concentration of potentially disturbing components. This is in particular advisable if a lysis agent was used in step a) that comprises phenol and/or a chaotropic agent. According to one embodiment, the DNase digest is performed in the absence of organic solvents in a concentration that would inactivate or disturb the activity of the DNase. Thus, if organic solvents are used in step a) that may disturb the activity of the DNase, they are removed by appropriate steps prior to step c) in order to obtain the degraded sample/lysate free of contaminating amounts of contaminating agents that could prevent DNase digestion. Alternatively or additionally, the organic solvent can be diluted down to concentrations which do not disturb or prevent the activity of the DNase. Furthermore, also chaotropic agents can disturb the activity of the DNase, if they are present in higher concentrations. Therefore, according to one embodiment the DNase digest in step c) is performed in the absence of chaotropic agents in a concentration that inactivate or disturb the activity of the DNase. Thus, if chaotropic agents are used in step a), their concentration preferably does not exceed 2M, 1.5M, 1M or preferably, do not exceed 0.75M in the DNase reaction composition during the DNase digest performed in step c). If high concentrations of chaotropic agent(s) and/or organic solvent(s) are used in step a) that could accordingly, result in higher concentrations during the DNase digest, their concentration can be lowered for the DNase digest by adding e.g. a dilution solution or water to the degraded sample. If using a proteolytic enzyme such as a protease in step a), said proteolytic enzyme can digest the DNase if the proteolytic enzyme is still active when performing the DNase digestion on the degraded sample. However, it was found (see the examples) that a DNase digest is surprisingly still possible even if using a proteolytic enzyme in step a). To optimize the performance of the DNase digest when using a proteolytic enzyme in step a), it is advantageous to perform the degradation step a) using the proteolytic enzyme in a concentration and/or for an incubation time so that the proteolytic enzyme, which usually also digests itself, has a reduced or even no activity at the time the DNase is added. Furthermore, it is also within the scope of the present invention to inactivate the proteolytic enzyme, e.g. by heat inactivation or by adding a protease inhibitor such as e.g. AEBSF (4-(2-Aminoethyl)-benzensulfonylfluorid), PMSF (Phenylmethylsulfonylfluorid Leupeptin N-acetyl-L-leucyl-L-leucyl-L-argininal and aprotinin. The protease inhibitor should inhibit the activity of the proteolytic enzyme that is used for degrading the sample in step a). Preferably, protease inhibition is irreversible. Thereby, the performance of the DNase digest can be improved. However, the examples show that the DNase digest according to the present invention surprisingly also works highly efficient even if the proteolytic enzyme is not inactivated in advance. Thus, according to one embodiment, no protease inhibitor is added to the degraded sample comprising the proteolytic enzyme.

The DNase digest is performed in the presence of Mg and Ca ions in concentrations at which the DNase is active. E.g. for performing the DNase digest, Mg and Ca ions can be added to the degraded sample e.g. in form of $MgCl_2$ and $CaCl_2$ to establish suitable concentrations in the DNase digestion mixture which comprises the degraded sample. The suitable concentrations of Mg and Ca ions depend on the composition of the degraded sample and in particular the lysis conditions that were used in degradation step a). E.g. if Ca and Mg ions were already provided during degradation and thus, are present in the degraded sample, less amounts of Mg and Ca ions can be added during step c) or the addition of Mg and Ca is not even necessary. The use of higher concentrations of Mg and Ca ions during the DNase digest is e.g. advisable, if chelating agents such as e.g. EDTA were used during degradation step a), in particular if they were used in higher concentrations, because chelating agents such as EDTA can inhibit the DNase by complexing Mg ions. Surprisingly, it was found that not only higher Mg ion concentrations, but in particular higher Ca ion concentrations have a positive influence on the activity of the DNase when performing the DNase digest on the degraded sample. In particular, an increase in the Ca ion concentration was seen to improve the DNase digest, most likely due to a protection of the DNase from degradation by proteolytic enzymes such as proteases. According to one embodiment, the Mg ions and the Ca ions are provided in the reaction composition, preferably in the form of $MgCl_2$ and $CaCl_2$, in a concentration selected from the group consisting of at least 0.2 mM each, at least 2 mM each, at least 5 mM each, at least 7.5 mM each and preferably at least 10 mM each. Furthermore, the Ca ion can be provided in the DNase digest reaction composition in a concentration range that is selected from the group consisting of 0.2 mM to 1 M, 2 mM to 500 mM, 5 mM to 100 mM and 10 mM to 50 mM. Furthermore, the Mg ion can be provided in the DNase digest reaction composition in a concentration range that is selected from the group consisting of 0.2 mM to 1M, 2 mM to 500 mM, 2 mM to 100 mM and 10 mM to 50 mM. Lower Mg and Ca ion concentrations may also be used, in particular if no chelating agents are present in the DNase digest reaction composition, if no proteolytic enzyme was used in degradation step a) and/or if the proteolytic enzyme used in step a) was inactivated, e.g. by adding a protease inhibitor.

The DNase digest reaction composition comprising the DNase, the degraded sample and optionally, further additives that promote the DNase digest is incubated for a suitable time to allow the DNA to be degraded. The incubation time depends on the amount of DNase used, the amount of DNA present in the degraded sample that is subjected to the DNase digest (and accordingly the sample type and whether intermediate steps were performed in advance to reduce the amount of DNA; see above). Preferably, the incubation with the DNase occurs for at least 1 min to 6 h, at least 5 min to 120 min, at least 10 min to 60 min or at least 15 min to 30 min. The temperature for incubation and the reaction conditions should be chosen according to the recommendations for the specific DNase used. Preferably, incubation is performed in a temperature range of 10-50° C., preferred 15° C. to 37° C., more preferred 20-25° C. The DNase digest can usually be performed at room temperature. Performing the DNase digest at room temperature or below has the advantage that a proteolytic enzyme, if present in the DNase digest reaction composition, is less active because proteolytic enzymes, in particular proteases such as proteinase K, are more active at higher temperatures.

Step d) of the method according to the present invention comprises the isolation of the RNA from the DNase digested sample. For this purpose, basically any RNA isolation method known in the prior art can be used which allows to isolate the RNA from the DNase digested sample. Usually, after performing a DNase digestion, the RNA is provided in an aqueous composition. Thus, basically any method known in the prior art for isolating RNA from an aqueous composition can be used. E.g., the RNA can be isolated from the DNase digested sample by adding at least one alcohol to said aqueous phase, thereby precipitating the RNA. The respectively precipitated RNA can e.g. be recovered by centrifugation of the aqueous phase and decanting the supernatant liquid. The pellet can be optionally washed and dissolved in an appropriate solution/buffer to render the purified RNA. If special sample types are processed, such as e.g. cross-linked samples, special intermediate steps might be necessary to ensure a good RNA recovery. E.g., when processing a cross-linked sample a special heating step is usually performed to reverse at least a portion of the cross-links prior to isolating the RNA.

According to a preferred embodiment, step d) comprises establishing binding conditions by adding appropriate additives to the DNase digested sample and binding the RNA to a nucleic acid binding solid phase. Suitable additives that promote binding include but are not limited to alcohols, chaotropic agents and detergents. Suitable nucleic acid binding solid phases and corresponding suitable binding conditions are known in the prior art.

According to a preferred embodiment, step d) comprises at least the following steps:
d.1) adding at least one alcohol and/or at least one chaotropic agent and optionally further additives to the DNase treated sample to form a binding mixture and contacting the binding mixture with a nucleic acid binding solid phase to bind the RNA to said solid phase;
d.2) optionally washing the RNA while it is bound to the solid phase;
d.3) optionally eluting the RNA from the solid phase.

As nucleic acid binding solid phase, any material that is capable of binding nucleic acids can be used and thus includes a variety of materials that are capable of binding nucleic acids under suitable conditions. Exemplary solid phases that can be used in conjunction with the present invention include, but are not limited to, compounds comprising silica and siliceous solid phases, including but not limited to, silica particles, silicon dioxide, diatomaceous earth, glass, alkylsilica, aluminum silicate, and borosilicate; nitrocellulose; diazotized paper; hydroxyapatite (also referred to as hydroxyl apatite); nylon; metal oxides; zirconia; alumina; polymeric supports, diethylaminoethyl- and triethylaminoethyl-derivatized supports, hydrophobic chromatography resins (such as phenyl- or octyl Sepharose) and the like. The term solid phase is not intended to imply any limitation regarding its form or design. Thus, the term solid phase encompasses appropriate materials that are porous or non-porous; permeable or impermeable; including but not limited to membranes, filters, sheets, particles, magnetic particles, beads, gels, powders, fibers, and the like. According to one embodiment, the surface of the solid phase is not modified and is, e.g., not modified with functional groups. According to a preferred embodiment, the nucleic acid binding solid phase is comprised in a column. The term "column" as used herein in particular describes a container having at least two openings. Thereby, a solution and/or sample can pass through said column. The term "column" in particular does not imply any restrictions with respect to the shape of the container which can be e.g. round or angular and preferably is cylindrical. However, also other shapes can be used, in particular when using multi-columns. The column comprises the nucleic acid binding solid phase. Said solid phase that is comprised in said column should allow the passage of a solution, respectively the sample when applied to the column. This means that if e.g. a centrifuge force is applied to the column, a solution and/or the sample is enabled to pass through the column in direction of the centrifuge force. As discussed above, when using a respective column based nucleic acid isolation procedure, the sample is usually passed through the column, e.g. assisted by centrifugation or vacuum, and the nucleic acids bind to the comprised nucleic acid solid phase during said passage. The column can be used in a single format or in a multi-format. Such multi-columns having a similar format as multi-well plates and which comprise a nucleic acid binding solid phase such as a membrane, are well-known in the prior art. Preferably, the column is a spin column. As nucleic acid binding solid phase comprised in the column, any solid phase can be used that is usually utilized in column based nucleic acid isolation procedures. Preferably, a nucleic acid binding membrane, and thus a membrane that is capable of binding nucleic acids is used in step a). Suitable membranes include but are not limited to hydrophilic membranes, hydrophobic membranes and membranes which bind nucleic acids via ion exchange. Examples include but are not limited to silica membranes, glass fiber membranes, nylon membranes, cellulose membranes such as nitrocellulose membranes, modified cellulose membranes (e.g. acetyl- or hydroxy-), paper membranes, in particular modified papers. Preferably, the membrane is porous. Furthermore, it is preferred to use a membrane comprising or consisting of silica. A further common nucleic acid binding solid phase comprised in a column is a fill of nucleic acid binding particles, such as silica particles, or a layer of a nucleic acid binding material (e.g. a silica gel). E.g. the silica particles can be arranged as a layer on an inert filter or membrane, thereby forming a nucleic acid binding solid phase. To alleviate the passage of the sample through the nucleic acid binding solid phase comprised in the column, suitable means can be used in step d) such as e.g. centrifugation or the use of a pressure difference-generating apparatus which e.g. presses the sample through the column, respectively the nucleic acid binding solid phase or sucks it through the nucleic acid binding solid phase by applying a vacuum. Respective means are well known in the prior art and thus need no further description here.

As alcohol that can be used to establish the binding conditions, it is preferred to use short chained branched or unbranched alcohols with preferably one to 5 carbon atoms. Examples are methanol, ethanol, propanol, isopropanol and butanol. Also mixtures of alcohols can be used. The alcohol is preferably selected from isopropanol and ethanol because said alcohols are in particular effective to precipitate RNA and/or allow binding of the alcohol to the solid phase. The concentration of alcohol used for isolating the RNA from the DNase digested sample depends on whether it is intended to include small RNAs in the isolated total RNA or not. In case it is intended to also purify small RNAs such as miRNAs, it is recommended to use higher alcohol concentrations. If it is not desired to include respective small RNA species in the isolated total RNA, lower alcohol concentrations are preferred. The concentration of alcohol when mixed with the DNase treated sample (and optionally, further additives) may lie in a range of 10% v/v to 90% v/v in the resulting mixture. For isolating total RNA including small RNA, it is beneficial to use an alcohol concentration of ≥40% v/v, preferably ≥50% v/v, more preferred ≥60% v/v, most preferred ≤70% v/v. In case it is not desired to include small RNAs, the concentration of alcohol is preferably ≤40% v/v. Thus, the concentration may be selected from the group consisting of at least 20%, at least 30% v/v, at least 40% v/v, at least 50% v/v, at least 60% and at least 70% v/v when mixed with the DNase treated sample (and optionally, further additives). Preferably, the alcohol concentration lies in a range of 20% v/v to 90% v/v/ or 30% v/v to 85%, preferably in the range of 30% v/v to 70% v/v when mixed with the DNase treated sample (and optionally, further additives).

According to one embodiment, binding is assisted by adding a chaotropic agent to the DNase digested sample in addition to the alcohol. The concentration of chaotropic agents used during binding and thus in the binding mixture may lie in a range of 0.05M up to the saturation limit. Preferred concentration ranges lie, depending on the chaotropic agent used, within 0.1M to 7M, 1M to 7M, 1.5M to 6M and 2M to 4M. Suitable chaotropic agents and in particular chaotropic salts are also described above and include but are not limited to guanidinium hydrochloride, guanidinium thiocyanate, guanidinium isothiocyanate, sodium thiocyanate, sodium iodide, sodium perchlorate, sodium trichloroacetate and sodium trifluoroacetate. Basically the same chaotropic agents can be used for degradation/lysis and binding.

Furthermore, at least one detergent, preferably a non-ionic detergent may be added to improve the binding conditions. Adding a detergent can improve binding, because the detergent can solubilize any protein remainders, including the DNase, which can potentially reduce the binding of the RNA to the solid phase. Said detergent is preferably comprised in the binding mixture in a concentration of 0.1% to 10%, preferred 1-5%. Also a mixture of detergents can be used.

The pH value used for binding the RNA to the solid phase preferably lies in a range of 4 to 9, preferably in a range of about 5 to 8, most preferred 6 to 7.5.

According to one embodiment, one or more washing steps are performed in step d2) while the RNA is bound to the solid phase. For this purpose common washing solutions may be used. It is recommended to use washing solutions which do not result in a release of the RNA, in particular the small RNA if small RNA shall be recovered, from the nucleic acid binding solid phase. According to one embodiment, the solution used for washing comprises at least one chaotropic agent, at least one alcohol and/or at least one buffering component. It may also comprise a detergent. Examples of respective chaotropic salts are alkali salts like sodium perchlorate, sodium trichloroacetate and sodium trifluoroacetate. As alcohol, short chained branched or unbranched alcohols with preferably one to 5 carbon atoms can be used for washing, respectively in the washing solution. Examples are methanol, ethanol, propanol, isopropanol and butanol. Preferably, isopropanol and/or ethanol are used. Preferably, ionic and/or non-ionic detergents are used as detergent. Preferably, a non-ionic detergent is used in a concentration of at least 0.1%. A further suitable washing solution which can be used alternatively or also in addition (preferably subsequently) to the washing solutions described above comprises an alcohol and a biological buffer. Suitable alcohols and biological buffers are described above. Preferably, isopropanol or ethanol, most preferred ethanol is used for a second washing step. Preferably, ethanol is used in a concentration of at least 30% v/v, preferably at least 50% v/v, more preferred at least 70%. The biological buffer is preferably Tris at a pH of approx. 7 to 8. However, also other buffers such as sodium citrate and also other pH values can be used.

The term "RNA" as used herein, in particular refers to a polymer comprising ribonucleosides that are covalently bonded, typically by phosphodiester linkages between subunits. The term RNA in particular refers to NhnRNA; mRNA; noncoding RNA (ncRNA), including but not limited to rRNA, tRNA, miRNA (micro RNA), siRNA (small interfering RNA), snoRNA (small nucleolar RNA), snRNA (small nuclear RNA) and stRNA (small temporal RNA); fragmented or degraded RNA; viral RNA, extracellular RNA and the like. The terms "RNA" and "RNAs" are used herein as synonyms. The term "small RNA" or "small RNAs" (these terms are also used as synonyms) in particular refers to small RNA. The term "small RNA" in particular refer to RNA having a length of less than 1000 nt, 500 nt, 400 nt, 300 nt, 100 nt or 70 nt and include but are not limited to miRNA, siRNA and other short interfering nucleic acids, snoRNAs, snRNAs, tRNA, piRNA, tnRNA, small rRNA, hnRNA, circulating nucleic acids, fragments of RNA, degraded RNA, ribozymes, viral RNA, RNA of infectious origin, artificial RNA such as ribo oligonucleotides. Furthermore, the expression "RNA including small RNA" not only refers to total RNA which comprises portions of small target nucleic acids but also refers to and encompasses RNA which consists of small RNA and accordingly, which do not comprise larger RNA molecules.

The term "sample" is used herein in a broad sense and is intended to include a variety of sources and compositions that contain nucleic acids. The sample may be a biological sample but the term also includes other, e.g. artificial samples which comprise nucleic acids. Exemplary samples include, but are not limited to, whole blood; blood products such as plasma or serum; red blood cells; white blood cells; buffy coat; swabs, including but not limited to buccal swabs, throat swabs, vaginal swabs, urethral swabs, cervical swabs, throat swabs, rectal swabs, lesion swabs, abscess swabs, nasopharyngeal swabs, and the like; urine; sputum; saliva; semen; lymphatic fluid; amniotic fluid; cerebrospinal fluid; peritoneal effusions; pleural effusions; fluid from cysts; synovial fluid; vitreous humor; aqueous humor; bursa fluid; eye washes; eye aspirates; pulmonary lavage; lung aspirates; tissues, including but not limited to, liver, spleen, kidney, lung, intestine, brain, heart, muscle, pancreas, cell cultures, plant tissues or samples, as well as lysates, extracts, or materials and fractions obtained from the samples described above or any cells and microorganisms and viruses that may be present on or in a sample and the like. Materials obtained from clinical or forensic settings that contain nucleic acids are also within the intended meaning of the term "sample". Preferably, the sample is a biological sample derived from a human, animal, plant, bacteria or fungi. Preferably, the sample is selected from the group consisting of cells, tissue, bacteria, virus and body fluids such as for example blood, blood products such as buffy coat, plasma and serum, urine, liquor, sputum, stool, CSF and sperm, epithelial swabs, biopsies, bone marrow samples and tissue samples, preferably organ tissue samples such as lung, kidney or liver. Furthermore, the skilled artisan will appreciate that lysates, extracts, or processed materials or portions obtained from any of the above exemplary samples are also within the scope of the term "sample". The term "sample" also includes processed samples such as preserved, fixed and/or stabilised samples. However, according to one embodiment, the sample is not a sample which is fixed by cross-linking, herein also referred to as a cross-linked sample, and in particular, is no FFPE sample.

As the method allows isolating RNA including small RNA with an reduced amount of DNA contaminations, the method according to the present invention is particularly useful for isolating RNA from samples containing degraded or compromised RNA. Non-limiting examples of such samples include cell containing samples that have been preserved, e.g. formalin fixed and paraffin-embedded (FFPE samples) or other samples that were treated with cross-linking fixatives such as e.g. glutaraldehyde. E.g. biopsy samples from tumors are routinely stored after surgical procedures by FFPE, which may compromise DNA and/or RNA integrity. Respective degraded nucleic acids often have a small size and thus are small nucleic acids. The disclosed method may be advantageously used for isolating RNA which consist of or comprise small target nucleic acids. E.g. the sample may be a sample which comprises small nucleic acids such as non coding RNA (e.g. snoRNAs or miRNA). Furthermore, the RNA may consist of or may comprise modified or degraded RNA. The modification or degradation can be e.g. due to treatment with a preservative(s).

Thus, according to one embodiment, the RNA is isolated from a sample that is fixed by cross-linking. Here, basically any method suitable for isolating RNA from cross-linked samples can be used, however, performing the DNase digest according to the present invention prior to isolating the RNA from the degraded sample. According to one embodiment, isolating RNA from a sample that is fixed by cross-linking comprises at least the following steps:
  a) degrading the sample;
  b) optionally separating undissolved constituents from the degraded sample;
  c) incubating at least a portion of the degraded, optionally further processed sample with a DNase; and
  d) isolating the RNA from the DNase treated sample,
wherein at least cross-links of, respectively involving the RNA are reversed prior to isolating the RNA.

Details with respect to the degradation step a) are described above. When degrading a cross-linked sample, it is preferred to use a proteolytically active compound, in particular a proteolytically active enzyme such as a protease, in order to degrade the sample. Suitable conditions are described in detail above. For cross-linked samples, it can be advantageously to use longer incubation times in order to ensure that the cross-linked sample is efficiently degraded and the RNA is efficiently released. However, also a partial digestion of the cross-linked sample in step a) can be advantageous as will be explained in detail below. Isolating RNA from a cross-linked sample usually requires the reversal of the cross-links in the RNA prior to isolating the RNA. This can be achieved by heating the sample in the presence of a nucleophilic reagent as is known in the prior art and as will be explained below. Preferably, said heating step to reverse the cross-links is performed after degrading the sample in step a) and prior to performing the DNase digestion step c). After performing the DNase digestion step according to the present invention, the RNA can then be isolated from the DNase treated sample. For this purpose, common RNA isolation methods can be used as are also described above. It is referred to the above disclosure.

According to a preferred embodiment when processing a cross-linked sample, degradation step a) of the method according to the present invention comprises the partial degradation of the sample by partial proteolysis of the protein-containing components of the sample using at least one proteolytically active compound to selectively release the RNA into a dissolved fraction of the sample, while the DNA predominantly remains in the undissolved fraction of the sample. This partial degradation allows to obtain separate fractions, wherein the dissolved fraction comprises mainly RNA and the undissolved fraction comprises mainly DNA. That this separation is possible is most likely due to the different effects of the cross-linking on RNA and DNA. During degradation of the cross-linked sample using a proteolytically active compound, RNA is released more easily and thus quicker into the dissolved fraction than DNA, which remains longer in the undissolved fraction of the sample. This allows to separate a mainly RNA containing dissolved fraction, from a mainly DNA containing undissolved fraction.

According to one embodiment when processing a cross-linked sample, the degradation step a) has one or more, preferably all, of the following characteristics:
 i) it comprises adding an aqueous buffer solution to the sample;
 ii) a proteolytic enzyme is used for partial or complete proteolysis; and/or
 iii) it comprises heating the sample.

Suitable aqueous buffer solutions that can be used to degrade the sample, respectively which assist degrading, were described above. It is referred to the above disclosure. Furthermore, suitable and preferred proteolytic enzymes that can be used in step a) as well as suitable heating conditions and incubation times that can be used when using a proteolytic enzyme were described above. For achieving an efficient release of the RNA while keeping the DNA in the undissolved fraction, it is preferred to incubate the sample in step a) in the presence of a proteolytic enzyme, preferably proteinase K, and an aqueous buffer solution which preferably comprises at least one detergent, in particular an anionic detergent such as SDS, and a buffering agent, for a time period between 5 min and 90 min, preferably 10 min to 30 min. Furthermore, incubation can be assisted by heating, preferably to a temperature of at least 30° C. to the maximum temperature under which the proteolytic enzyme is active, preferably a temperature range between 40° C. to 70° C., more preferred 50° C. to 65° C. is used. These temperature ranges are particularly suitable when using proteinase K as proteolytic enzyme. These conditions are also particularly suitable to selectively release RNA from the cross-linked sample, while keeping most of the DNA in the undissolved fraction. If a respective partial digestion is not intended, longer incubation times can be used (e.g. up to 24 h, up to 12 h, up to 5 h or up to 3 h) in order to completely digest the sample and to release the comprised nucleic acids.

According to one embodiment, after performing the digest with the proteolytically active compound, which preferably is a proteolytic enzyme, at least a portion of the cross-links is reversed by heating the degraded sample, preferably to a temperature of at least 60° C., more preferred at least 70° C., more preferred at least 80° C., most preferred at least 90° C. Heating is preferably performed in the presence of a nucleophilic reagent as is described in WO2007/068764, herein incorporated by reference. The nucleophilic reagent can be provided any time prior to heating and thus, can be contained e.g. in the aqueous buffer solution used during step a) or can be added afterwards. Suitable heating periods are also described in WO2007/068764. According to one embodiment, heating is performed for a time period of at least 5 min, preferably at least 10 min, most preferred at least 15 min. Suitable incubation ranges include but are not limited to 5 min to 5 h, 10 min to 3 h, 10 min to 2 h, 10 min to 1 h and 10 min to 30 min. Longer incubation times and higher incubation temperatures result in a more efficient de-crosslinking and thus a higher RNA yield but have the risk that the RNA can become fragmented. Thus, the incubation time and temperature should be chosen considering the intended down-stream application of the purified RNA. This reversal of the cross-links is usually performed prior to performing the DNase digest in step c).

If making use of the partial degradation in step a) to separate the mainly RNA containing dissolved fraction from the mainly DNA containing undissolved fraction, this additional heating step to reverse the cross-links can e.g. be performed before, or after separating the dissolved fraction from the undissolved fraction. If it is intended to isolate the DNA subsequently from the undissolved fraction, it is preferred to perform said heating step after separating the fractions (as it is described subsequently) because this heating step can result in that further DNA is released from the undissolved fraction. If it is only intended to isolate the RNA, said heating step may also be performed prior to separating the fractions, because additionally released DNA would be degraded by the DNase digest performed in step c) and this heating step prior to separating the fractions can have a positive influence on the RNA yield.

If making use of the partial degradation in step a) to separate the mainly RNA containing dissolved fraction from the mainly DNA containing undissolved fraction, step b) of the method according to the present invention comprises separating the mainly RNA containing dissolved fraction from the mainly DNA containing undissolved fraction. Using a suitable separation process, for example centrifugation, it is possible to separate, after the incomplete "digestion" of the cross-linked sample, a still undissolved fraction comprising DNA from the RNA-comprising dissolved fraction, which can have the form of a supernatant. The dissolved fraction comprises mainly RNA, based on the total amount of nucleic acids in the dissolved fraction (at least 50%, preferably at least 70%, more preferred at least 80%, most preferred at least 90%) and the undissolved residue comprises mainly DNA (at least 50%, preferably at least 70%, more preferred at least 80%, most preferred at least 85%), based on the total amount of nucleic acids in the undissolved residue, respectively fraction.

The separation of the two fractions into a dissolved fraction and an undissolved fraction can be carried out using any method known to the person skilled in the art as being suitable for separating liquid and solid components, such as, for example, filtration, sedimentation, decantation, centrifugation, etc. According to a preferred embodiment, the separation of the dissolved fraction comprising predominantly RNA from the undissolved fraction comprising predominantly DNA requires neither precipitation nor extraction of one or both types of nucleic acid with organic solvents nor selective binding of one or both types of nucleic acid to a solid matrix. The mainly DNA containing undissolved fraction obtained in this separation step is also referred to as pellet, where, for the purpose of the present application, this term is explicitly not limited to an undissolved fraction separated off from the liquid component of the sample by centrifugation, but also includes undissolved residues separated off by other means, for example the solid material that remains on the filter after a filtration. It is preferred though that separation results in that the mainly DNA containing undissolved fraction is obtained in form of a compact pellet, because this allows to easily separate the mainly DNA containing pellet from the mainly RNA containing dissolved fraction.

According to a particularly preferred embodiment when processing a cross-linked sample and making use of the partial digestion in step a), separation is assisted by cooling the degraded sample either prior to or during separation. Thus, the separation of the undissolved fraction from the dissolved fraction preferably is supported by cooling the mixture after the reaction time of the proteolytic enzyme, in particular if degradation is carried out at elevated temperatures, i.e. temperatures above room temperature. Cooling is preferably carried out by incubating the partially degraded sample at a temperature below the temperature of the digestion with the proteolytic enzyme, preferably at or below room temperature, in particular at 15° C. or less, 10° C. or less, 4° C. or less or at even lower temperatures such as, for example, −20° C. or −80° C. Cooling at these very low temperatures is preferably brief to avoid freezing of the entire aqueous solution. Cooling has the advantage that the separation of the undissolved fraction, in particular the pelleting, is more efficient. This is in particular advantageous because cross-linked samples such as FFPE samples usually comprise undissolved components, in particular DNA being cross-linked to proteins, rather than large amounts of solid components. Said undissolved components are usually difficult to pellet. Cooling assists the pelleting of the undissolved components and thus makes the separation more efficient. Thus, cooling results in that the mainly DNA containing undissolved fraction comprises more DNA and accordingly, the RNA containing dissolved fraction comprises less DNA contamination due to the improved separation of the individual fractions. This is particularly advantageous when processing cross-linked samples comprising little cell material. According to one embodiment, separation results in that the mainly DNA containing undissolved fraction is obtained in form of a compact pellet. This allows to easily separate the mainly DNA containing pellet from the mainly RNA containing dissolved fraction.

According to one embodiment, the separated, mainly RNA containing dissolved fraction of the sample is used in step c) for performing the DNase digest. As discussed above, the cross-links are preferably reversed in the mainly RNA containing dissolved fraction prior to performing the DNase digest. Suitable and preferred conditions for reversing cross-links and performing the DNase digest were described in detail above. This embodiment has several advantages, because separating the undissolved fraction which comprises the main amount of the DNA comprised in the cross-linked sample already removes the main portion of the DNA comprised in said sample. Thus, the RNA containing dissolved fraction is DNA depleted. Remaining amounts of DNA that were already released during the partial digestion in step a) are then efficiently degraded by the DNase digest performed in step c) according to the method of the present invention. Thus, pure RNA is provided with high yield which comprises little to no DNA contaminations.

According to one embodiment, the sample fixed by cross-linking is a paraffin-embedded sample, preferably a formalin-fixed paraffin-embedded sample (FFPE sample). Here, it is preferred that the method comprises prior to step a) a step i) for the removal of the paraffin, preferably by bringing the sample into contact with a hydrophobic organic solvent, particularly preferably using an apolar aliphatic or aromatic hydrocarbon of a chain length of more than 6 and less than 17 carbon atoms or mixtures of these, optionally with addition of a $C_1$-$C_5$-alcohol; in particular a hydrocarbon or hydrocarbon mixture selected from the group comprising xylene, heptane and mineral oil, optionally with addition of 1-25% by volume of methanol. Further deparaffinization methods are also well-known in the prior art and thus, need no further description. Suitable deparaffinization solutions are also commercially available with detailed instructions. Other entparaffinization methods include melting, wherein the cooled paraffin is collected on top of the aqueous phase or at the side of the tube.

According to one embodiment, the method comprises, after removal of the paraffin according to step i) and before the degradation of the sample according to step (a), optionally one or more of the following steps:
ii) rehydration of the sample, preferably by repeated washing of the sample with aqueous $C_1$- to $C_5$-alcohol solutions of successively increasing water content,
iii) drying of the sample and/or
iv) homogenization of the sample.

Respective method steps to work up the deparaffinised sample are also well-known in the prior art and thus, need no further description here.

According to one embodiment, the RNA and DNA containing sample is obtained in form of a pellet after deparaffinization. Preferably, an aqueous buffer solution is added to said pellet for performing the degradation step a). According to a further embodiment, the RNA and DNA containing sample is obtained after mixing the deparaffinised sample with an aqueous buffer solution, preferably the aqueous buffer solution for use in step a) (see above description for suitable and preferred embodiments), thereby forming an aqueous RNA and DNA containing phase which is degraded in step a) of the method according to the present invention. E.g. as described above, it can be subjected in step a) to partial proteolysis of the protein-containing components of the sample using at least one proteolytically active compound to selectively release the RNA into an dissolved fraction, while the DNA predominantly remains in the undissolved fraction. Here, the proteolytically active compound, preferably the proteolytic enzyme, can be added to the aqueous phase while the solution used for deparaffinization is still on top of the aqueous phase that was formed due to the addition of the aqueous buffer solution. The same applies when using a complete digest/degradation in step a). If performing the separation step b) in this alternative e.g. by centrifuging the partially digested cross-linked sample (see above), the mainly DNA containing undissolved fraction will form a pellet within the aqueous phase. To separate the dissolved from the undissolved fraction, the aqueous phase is collected through the deparaffinisation solution e.g. by using a pipette, while leaving the undissolved, mainly DNA containing pellet behind. Alternatively, the deparaffinisation solution can be separated in advance from the aqueous phase that is obtained after the addition of the aqueous buffer solution before adding the proteolytically active compound.

The mainly DNA containing undissolved fraction can be discarded, if only RNA is supposed to be obtained. However, said undissolved fraction, which comprises the DNA and other undissolved components of the incompletely digested sample, can also be used for isolating the DNA. Here, it is possible to use any methods suitable or according to the state of the art customary for isolating DNA from fixed samples, since the pellet still has essentially the properties of a fixed sample (see e.g. WO2007/068764, WO2008/021419, WO2005/012523 and WO2005/054466 or commercially available products such as QIAamp DNA FFPE Kits). In particular, the preceding incomplete protease digestion has not removed any substantial amounts of DNA from the sample and/or has not removed DNA crosslinks in any significant amount. To this end, another or an additional enzymatic protease digestion is advantageously carried out to lyse the sample completely, followed by heat incubation to reverse the cross-links. Said heating can be performed in a nucleophile-containing solution such as described, for example, in WO 2007/068764. The DNA released in this manner can then be purified further with the aid of any suitable DNA isolation method, for example by binding to a silica matrix using, for example, the QIAamp FFPE Kit (QIAGEN). Thus, according to one embodiment, the DNA is obtained from the undissolved, mainly DNA containing fraction after separation of the fractions.

Thus, according to one embodiment, the DNA is obtained from the undissolved, mainly DNA containing fraction after separation of the fractions. Obtaining the DNA from the undissolved fraction may comprise the following steps:

i) releasing the DNA from the undissolved, mainly DNA containing fraction by subjecting said undissolved fraction to lysis with simultaneous enzymatic protease digestion, wherein preferably, at least one detergent is used during lysis and optionally, further additives; suitable methods are known in the prior art and suitable conditions are also described above;
  ii) heating the mainly DNA containing fraction to at least partially reverse the cross-links preferably by heating the sample preferably after step i) to a temperature of at least 70° C., more preferred at least 80° C., most preferred at least 85° C., more preferred at least 90° C., preferably in the presence of a nucleophilic reagent (see e.g. WO 2007/068764), preferably for at least 1 h, more preferred for at least 1.5 h, most preferred for at least 2 h; and
  iii) isolating the DNA after reversing the cross-links, preferably by establishing binding conditions by adding appropriate additives and binding the DNA to a nucleic acid binding solid phase. Preferably, a chaotropic agent and a detergent, preferably a non-ionic detergent, and alcohol are added to establish the binding conditions. Suitable examples for chaotropic agents, alcohols, detergents and nucleic acid binding solid phases are described above and can also be used when isolating the DNA. Suitable DNA isolating procedures are also well known in the prior art.

It is also within the scope of the present invention to perform additional, e.g. intermediate steps than the ones described herein. However, according to certain embodiments, no additional steps other than the ones described herein are performed.

Also provided is a method for isolating RNA, including small RNA from a RNA and DNA containing sample, wherein the sample is lysed and at least a portion of the optionally further processed lysate is incubated with a DNase to degrade DNA prior to purifying the RNA from the optionally further processed lysate. Preferably, the RNA is isolated from the lysate by binding it to a nucleic acid binding solid phase, preferably a nucleic acid binding solid phase comprised in a column. Details with respect to
  a) suitable and preferred conditions to achieve lysis of the sample (see above, degradation step a);
  b) suitable steps for further processing the sample;
  c) suitable and preferred conditions for the DNase digest;
  d) suitable and preferred samples;
  e) suitable and preferred solid phases: and
  f) suitable and preferred binding conditions
are described above in conjunction with the method according to the first aspect of the present invention. Therefore, it is referred to the above disclosure which also applies here.

Furthermore, the methods according to the first and second aspect can also comprise a step for the analysis/detection of the isolated RNA. All analysis methods known to the person skilled in the art, for example amplification techniques such as RT-PCR, qRT-PCR, cDNA transcription and subsequent amplification and analysis methods, gel electrophoresis, blotting techniques, in particular Northern blotting, microarray analyses, RNA sequencing, or combinations thereof can be used for analyzing the RNA isolated by the process according to the invention.

EXAMPLES

Example 1: DNAse Treatment for Efficient miRNA Purification

For this experiment, FFPE samples from rat which had been stored at room temperature for different periods of time were used: brain (storage time about 5 months) and heart (storage time about 18 months). With the aid of a microtome, sections of a thickness of about 20 µm were prepared from these samples. In each case, one section per reaction was used. Components of the RNeasy FFPE kit and the QIAamp FFPE kit from QIAGEN were employed for the subsequent nucleic acid isolation from the FFPE sections with aid of the inventive process.

To compare the isolation of miRNA with the aid of the process according to the invention with a process established specifically for the purification of miRNA from FFPE samples, sections of the same samples were used for the isolation of miRNA with the miRNeasy FFPE kit according to the manufacturer's (QIAGEN) instructions and used as control samples.

The deparaffinized sample pellets obtained in this manner were treated with 150 µl of an aqueous solution comprising 20 mM Tris, 2 mM EDTA and 0.2% SDS (pH 7) and mixed with 10 µl of a proteinase K solution (>600 mAU/ml) as proteolytically active compound. This mixture was incubated at 56° C. with shaking at 1400 rpm for 15 min. To separate the mainly RNA containing dissolved fraction (A) from the mainly DNA containing undissolved fraction (B), the samples were initially cooled on ice for 3 min and then centrifuged. For further isolation of the RNA including miRNA, the supernatant (fraction A) was removed and the DNA containing pellet was discarded.

The supernatant was subsequently incubated at 80° C. for 15 min to reverse the cross-links. The sample was cooled at room temperature for five minutes, after which 20 µl of different buffers for facilitating DNase-activity (pretreatment buffers 1-5, see below), 15 μl water and 5 μl of DNAse I solution from QIAGEN were added. The following buffers were used for this experiment:
pretreatment buffer 1: 0.46 M Tris-HCl (pH 7.5), 114 mM NaCl, 114 mM MgCl$_2$, 114 mM CaCl$_2$
pretreatment buffer 2: 0.46 M Tris-HCl (pH 7.5), 114 mM MgCl$_2$, 114 mM CaCl$_2$
pretreatment buffer 3: 46 mM Tris-HCl (pH 7.5), 11.4 mM NaCl, 11.4 mM MgCl$_2$, 11.4 mM CaCl$_2$
pretreatment buffer 4: 20 mM Tris-HCl (pH 7.5), 100 mM MgCl$_2$, 10 mM CaCl$_2$
pretreatment buffer 5: 20 mM Tris-HCl (pH 7.5), 100 mM MgCl$_2$, 2.5 mM CaCl$_2$ The mixture was incubated at room temperature for 15 min. In order to isolate RNA incl. small RNAs like micro RNAs from the DNase digested sample 400 μl of a chaotropic buffer, for example RLT buffer from QIAGEN, were then added, the mixture was mixed with 1400 μl 96-100% ethanol, applied to a silica membrane, for example present in the RNeasy MinElute column from QIAGEN, and passed through the membrane by centrifugation at 14 000 rpm for 1 min. The silica membrane was washed twice with 500 μl of the alcohol-containing wash buffer RPE (QIAGEN). The membrane was dried by 5 minutes of centrifugation at 14 000 rpm, and the RNA was, after a 1-minute incubation, eluted by centrifugation by applying with 30 μl of water.

For comparison, the same samples were used for purification of RNA incl. small RNAs without DNAse pretreatment but with a common on-column DNAse treatment after binding the RNA onto the membrane. Deparaffinzation and proteinase K digestion were performed as described above. After that, 320 μl of a chaotropic buffer, for example RLT buffer from QIAGEN, were then added, the mixture was mixed with 1120 μl 96-100% ethanol, applied to a silica membrane, for example present in the RNeasy MinElute column from QIAGEN, and passed through the membrane by centrifugation at 14 000 rpm for 1 min. The silica membrane was washed with 350 μl of a wash buffer containing chaotropic reagents and ethanol, like buffer RWT (QIAGEN). 80 μl of a mixture comprising 10 μl DNase 1 and an appropriate DNAse buffer (e.g. buffer RDD (QIAGEN)) was applied then onto the membrane and incubated for 15 min at room temperature. After that the membrane was again washed with buffer RWT and washed twice with 500 μl of the alcohol-containing wash buffer RPE (QIAGEN). The membrane was dried by 5 minutes of centrifugation at 14 000 rpm, and the RNA was, after an 1-minute incubation, eluted by centrifugation by applying with 30 μl of water.

To analyze the RNA isolated in this manner, exemplary the RNA from brain was analyzed using an Agilent Bioanalyzer, which separates the RNA molecules depending on size. FIG. 1 shows the results of Bioanalyzer measurement. RNA from FFPE samples is always partly degraded and the extent of degradation is dependent on multiple factors like fixation, embedding and storage of the sample and the RNA extraction method. Therefore, the gel-like visualization of the RNA shows in all cases partly degraded RNA (see FIG. 1). The 28S rRNA is not and the 18S rRNA is only weekly visible. In addition, a lot of RNA fragments occur from the size of the 28srRNA band down to low molecular weights. The common on column DNAse treatment results in very low yields of the smallest RNA population incl. miRNA (see arrow). In contrast, DNAse pretreatment prior to column loading according to the present invention allows isolation of high amounts of the very low molecular weight RNAs. In order to determine efficiency of miRNA purification in particular, the purified RNA was analyzed for detection and quantitation of miRNA 16 using the miScript PCR System, according to the manufacturer's (QIAGEN) instructions by real-time RT-PCR. The mean values obtained from the ct values measured are shown in Table 1.

TABLE 1

| DNAse treatment | brain | Heart |
| --- | --- | --- |
| pretreatment buffer 1 | 18.30 | 20.03 |
| pretreatment buffer 2 | 18.17 | 19.39 |
| pretreatment buffer 3 | 18.17 | 20.43 |
| pretreatment buffer 4 | 18.25 | 20.06 |
| pretreatment buffer 5 | 18.63 | 19.91 |
| On-column DNase treatment | 20.33 | 21.49 |

In all cases, the ct values measured are lower in samples with DNAse pretreatment, whereas on-column DNAse treatment gives significant higher ct values. Lower ct values represent higher amounts of miRNA with a ct value difference of one indicating of about the double amount of detected miRNA. Thus, DNAse pretreatment before isolating the RNA significantly enhances miRNA purification efficiency over the on-column DNase digest according to the state of art.

Example 2: Isolation of RNA from Different Types of Tissue by the Process According to the Invention The samples used for this experiment were FFPE samples from rat which had been stored at room temperature for different periods of time: kidney (storage time about 5 months), liver (storage time about 24 months), heart (storage time about 24 months) and lung (storage time about 24 months). With the aid of a microtome, sections of a thickness of about 20 μm were prepared from these samples. In each case, one section per reaction was used. Components of the RNeasy FFPE kit and the QIAamp FFPE kit from QIAGEN were employed for the subsequent nucleic acid isolation from the FFPE sections with aid of the inventive process.

To compare the isolation of RNA with the aid of the process according to the invention with a process established specifically for the purification of RNA from FFPE samples, sections of the same samples were used for the isolation of RNA with the RNeasy FFPE kit according to the manufacturer's (QIAGEN) instructions and used as control samples.

Deparaffinization, rehydration and drying of the sections were carried out as described in Example 1. The deparaffinized sample pellets obtained in this manner were treated with 150 μl of an aqueous solution comprising 20 mM Tris, 2 mM EDTA and 0.2% SDS (pH 7) and mixed with 10 μl of a proteinase K solution (>600 mAU/ml) as proteolytically active compound. This mixture was incubated at 56° C. with shaking at 1400 rpm for 15 min. To separate the dissolved fraction (A) from the undissolved fraction (B), the samples were initially cooled on ice for 5 min and then centrifuged. For further isolation of the RNA, the supernatant (fraction A) was removed and the DNA containing pellet was discarded.

The supernatant was subsequently incubated at 80° C. for 15 min. The sample was cooled at room temperature for five minutes, after which 20 μl of a DNAse buffer (comprising, for example, 0.46 M Tris-HCl (pH 7.5), 114 mM NaCl, 114 mM MgCl$_2$, 114 mM CaCl$_2$), 15 μl of deionized water and 5 μl of DNAse I solution from QIAGEN were added, and the mixture was incubated at room temperature for 15 min. 400

μl of a chaotropic buffer, for example RLT buffer from QIAGEN, were then added, the mixture was mixed with ethanol, applied to a silica membrane, for example present in the RNeasy MinElute column from QIAGEN, and passed through the membrane by centrifugation at 14 000 rpm for 1 min. The silica membrane was washed twice with 500 μl of the alcohol-containing wash buffer RW2 (QIAGEN). The membrane was dried by 5 minutes of centrifugation at 14 000 rpm, and the RNA was, after a 1-minute incubation, eluted by centrifugation by applying with 30 μl of water.

To analyze the RNA isolated in this manner, the yield was determined by measuring the absorption at 260 nm. The mean values of the duplicate determinations are shown in Table 2.

TABLE 2

| Tissue | Yield [μg] | |
| --- | --- | --- |
| | Sample | Control |
| Lung | 9.1 | 8.2 |
| Liver | 2.7 | 2.6 |
| Kidney | 2.3 | 2.2 |
| Heart | 7.6 | 5.3 |

With the aid of the process according to the invention, it was possible to isolate RNA from all samples, where in all cases the yields obtained with the process according to the invention were comparable to or higher than those of the controls.

To examine the suitability of the RNA isolated by the process according to the invention for amplification analyses, the RNA was used in quantitative real-time RT-PCR assays. Identical volumes of the isolated RNA eluates were used in each case in duplicate determinations for detecting an amplicon of the madH7 transcript and the c-jun transcript. Amplification was carried out in a total volume of 25 μl with a mastermix suitable for real-time RT-PCR, such as, for example, the QuantiTect SYBRGreen RT-PCR kit from QIAGEN, according to the manufacturer's instructions. Amplification was carried out in a suitable real-time amplification instrument such as, for example, the ABI PRISM® 7900HT Sequence Detection System from Applied Biosystems (Carlsbad, Calif., USA). In addition, microRNA16 (miR16) was detected in the RNA eluates using the miScript PCR system, according to the manufacturer's (QIAGEN) instructions by real-time RT-PCR. The mean values obtained from the ct values measured are shown in Table 3.

TABLE 3

| | | Lung (24 months) | Liver (24 months) | Kidney (6 months) | Heart (24 months) |
| --- | --- | --- | --- | --- | --- |
| madH7 | sample | 24.9 | 26.1 | 22.8 | 28.2 |
| | control | 27.6 | 26.8 | 23.6 | 29.2 |
| c-jun | sample | 26.1 | 26.9 | 26.6 | 28.7 |
| | control | 28.2 | 27.2 | 26.7 | 29.7 |
| miR16 | sample | 17.4 | 19.0 | 20.8 | 19.9 |
| | control | 20.44 | 21.1 | 19.4 | 21.2 |

In all cases, the measured ct value of the sample processed according to the invention is comparable to that of the control sample or even lower, which indicates that more small RNA was comprised in the sample.

Example 3: DNAse Treatment for Efficient miRNA Purification from Cell Culture Samples For this experiment 1×10⁶ pelleted Jurkat cells, which were stored frozen until RNA purification were used in duplication with four different methods for purification of RNA including small RNAs (lysis methods A to D) according to the present invention:

Lysis Method A

Frozen pellets were shortly thawed and resuspended in 300 μl of lysis buffer A, a chaotropic buffer (for example RLT buffer from QIAGEN) by vortexing. The lysate was homogenized by adding it onto a QIAshredder column and centrifugation for 2 min at 14.000 rpm. The flowthrough was mixed with 1190 μl water and 10 μl proteinase K and incubated at 56° C. for 10 min. Then 150 μl of a DNAse pretreatment buffer (457 mM Tris-HCL, pH 7.5, 114 mM NaCl, 114 mM MgCl$_2$, 114 mM CaCl$_2$) and 30 μl DNase I solution (QIAGEN) were added to the sample, followed my mixing and 15 min incubation at room temperature. After addition of 1.5 volumes (=2520 μl) of 96-100% ethanol and mixing of the sample, the mixture was applied to a silica membrane (for example present in the RNeasy MinElute column from QIAGEN), and passed through the membrane by centrifugation at 14.000 rpm for 1 min. Applying the sample onto the membrane was repeated until the complete mixture was passed through the membrane. After the last spin, the silica membrane was washed once with 500 μl of the chaotrop- and ethanol-containing washing buffer RWT (QIAGEN) and twice with 500 μl of the alcohol-containing wash buffer RPE (QIAGEN). The membrane was dried by 2 minutes of centrifugation at 14.000 rpm, and the RNA was eluted twice by applying 40 μl of water, and a 1-minute incubation, by centrifugation for 1 min at 10.000 rpm.

Lysis Method B

Frozen cell pellets were briefly thawed and resuspended in 700 μl of phenol-containing QiaZol lysis buffer (QIAGEN) by vortexing. The lysate was loaded onto a QIAshredder column and centrifuged for 2 min at 14.000 rpm. The flowthrough was saved, 140 μl chloroform was added and the composition was thoroughly mixed for 15 sec, followed by 3 min incubation at room temperature. The sample was centrifuged for 15 min at 4° C. and 14.000 rpm. Approximately 350 μl of the upper aqueous phase were carefully transferred to a fresh tube and mixed with the same volume of water. Then, 70 μl DNAse pretreatment buffer (457 mM Tris-HCL, pH 7.5, 114 mM NaCl, 114 mM MgCl$_2$, 114 mM CaCl$_2$) and 30 μl DNase I Solution (QIAGEN) were added, and the resulting composition was carefully mixed. After 15 min incubation at room temperature, 1200 μl of 96-100% ethanol were added, and the RNA was purified as described above in conjunction with lysis method A.

Lysis Method C

Cell pellets were briefly thawed and resuspended in 300 μl of an aqueous lysis buffer comprising a detergent, such as PKD buffer (QIAGEN). The lysate was homogenized by applying it onto a QIAshredder column and centrifuged for 2 min at 14.000 rpm. The flowthrough was saved, substituted with 30 μl DNAse pretreatment buffer (457 mM Tris-HCL, pH 7.5, 114 mM NaCl, 114 mM MgCl$_2$, 114 mM CaCl$_2$) and 30 μl DNase I solution (QIAGEN), and the resulting composition was carefully mixed. Following 15 min incubation at room temperature, 180 μl of a chaotropic salt containing buffer, such as RLT buffer (QIAGEN) were added, and the composition was mixed. Then, 810 μl of 96-100% ethanol were added, again followed by mixing. The RNA was purified as described above in conjunction with lysis method A.

Lysis Method D

Cell pellets were thawed and resuspended in 290 μl of an aqueous lysis buffer comprising a detergent, such as PKD buffer (QIAGEN), which is suitable for proteinase K treatment. The lysate was homogenized by loading it onto a QIAshredder column, followed by centrifugation for 2 min at 14.000 rpm. The flowthrough was saved. 10 µl proteinase K (>600 mAU/ml) were added. The sample was mixed and incubated at 56° C. for 10 min with 450 rpm on a thermomixer. Then, 30 µl DNAse pretreatment buffer (457 mM Tris-HCL, pH 7.5, 114 mM NaCl, 114 mM MgCl$_2$, 114 mM CaCl$_2$) and 30 µl DNase I solution (QIAGEN) were added and the composition was carefully mixed. After 15 min incubation at room temperature, 180 µl of a chaotropic salt containing buffer, for example RLT buffer (QIAGEN) were added and the sample was mixed. For RNA precipitation, 810 µl of 96-100% ethanol were added, and the sample was mixed. The RNA was isolated as described above in conjunction with lysis method A.

As a control for each of the tested lysis methods, the same lysis protocols were performed, however, lacking the DNase pretreatment step according to the invention. Instead, a state-of-the-art on-column DNase treatment was used. In other words, the addition of DNase pretreatment buffer and DNase as well as the 15 min incubation at room temperature were omitted. Instead of the DNase pretreatment, the control samples were applied onto the silica membrane of the RNeasy columns, followed by a washing step with 350 µl of a chaotropic salt- and ethanol-containing washing buffer, such as RWT buffer (QIAGEN). Then, 80 µl of a mixture containing 70 µl of commercially available DNase-buffer RDD (QIAGEN) and 10 µl DNAse I (QIAGEN) were applied onto the silica membrane, followed by incubation for 15 min at room temperature. Following the on-column DNase treatment the control samples were washed once more with 350 µl of a chaotropic salt- and ethanol-containing washing buffer, such as RWT buffer (QIAGEN), followed by two washing steps with 500 µl of an alcohol-containing wash buffer, e.g. RPE (QIAGEN). The RNA was eluted as described above.

In order to determine the efficiency of miRNA purification, the purified RNA was analyzed for detection and quantitation of miRNA 29a using the miScript PCR System, according to the manufacturer's (QIAGEN) instructions by real-time RT-PCR. The mean values obtained from the ct values measured are shown in Table 4.

TABLE 4

|  | DNAse pretreatment | DNAse on column treatment |
| --- | --- | --- |
| lysis A | 29.1 | 30.2 |
| lysis B | 26.5 | 28.7 |
| lysis C | 26.9 | 30.1 |
| lysis D | 26.2 | 28.8 |

In all cases, the ct values measured are lower in samples with DNAse pretreatment according to the invention, whereas DNAse on-column treatment results in significant higher ct values. Lower ct values represent higher amounts of miRNA, in which a ct value difference of one is indicative of about the double amount of detected miRNA. Thus, DNAse pretreatment according to the invention significantly enhances miRNA purification efficiency over the method according to the state-of-art.

In order to also determine the efficiency of DNAse pretreatment, real-time RT-PCR analysis was carried out for the β-actin transcript. RT-PCR without adding reverse transcriptase (−RT) amplifies only not removed, contaminating DNA in the RNA eluate. RT-PCR including reverse transcriptase (+RT) amplifies cDNA derived from RNA, as well as contaminating DNA. Thus, the ct difference (Δct) between RT-PCR without (−RT) and with reverse transcriptase (+RT) shows the efficiency of DNAse removal. The ct differences between the mean −RT values and mean +RT values are shown in Table 5.

TABLE 5

|  | Δct DNase pretreatment | Δct DNase on-column treatment |
| --- | --- | --- |
| lysis A | 12.0 | 17.4 |
| lysis B | 15.7 | 18.3 |
| lysis C | 15.9 | 17.4 |
| lysis D | 18.7 | 16.3 | ct-Differences (=Δcts) higher than 10 indicate very low residual DNA content. Differences in delta cts higher than 10 can vary due to the extreme low ct-values measured in the −RT samples and do not represent significant differences for gene expression analysis. In all cases, with DNAse pretreatment according to the invention as well as using conventional on column DNAse treatment, DNA was efficiently removed from the RNA. Δcts higher than 10 indicate a very low residual DNA content.

Example 4: DNAse Treatment for Efficient miRNA Purification from Whole Blood Samples For this experiment, 500 µl whole blood samples were used in duplicates with four different methods for RNA purification, including small RNAs (lysis method A to D) according to the present invention. Prior to RNA purification, erythrocytes were lysed using the following process:

The 500 µl whole blood samples were mixed each with 2.5 ml of a hypotonic erythrocyte-lysis buffer, such as EL buffer (QIAGEN). The mixture was incubated for 10-15 min on ice, including 1-2 vortex mixing steps from time to time. Following the incubation the samples were centrifuged for 10 min at 400×g, and all of the supernatant was discarded. 1 ml of a hypotonic erythrocyte-lysis buffer, such as EL buffer (QIAGEN) was added to the pellet, followed by mixing by briefly vortexing of the sample and another centrifugation step for 10 min at 400×g. Again, the whole supernatant was discarded. The pellet containing the white blood cells was used for RNA purification according to the following methods A to D:

Lysis Method A

The pelleted white blood cells were resuspended by vortexing in 300 µl of a chaotropic lysis buffer, for example RLT buffer (QIAGEN). The lysate was homogenized by adding it onto a QIAshredder column and centrifugation for 2 min at 14.000 rpm. The flowthrough was mixed with 590 µl water and 10 µl proteinase K and incubated at 56° C. for 10 min. Then 90 µl of a DNAse pretreatment buffer (457 mM Tris-HCL, pH 7.5, 114 mM NaCl, 114 mM MgCl$_2$, 114 mM CaCl$_2$) as well as 30 µl DNase I solution (QIAGEN) were mixed with the sample and incubated for 15 min at room temperature. After addition of 1.5 volumes (=1530 µl) of 96-100% ethanol and mixing of the sample, the solution was applied to a silica membrane, for example present in the RNeasy MinElute column (QIAGEN), and passed through the membrane by centrifugation at 14.000 rpm for 1 min. Applying the sample onto the membrane was repeated until the complete mixtures was passed through the membrane. The silica membrane was washed once with 500 µl of the chaotrop- and ethanol-containing washing buffer RWT (QIAGEN) and twice with 500 µl of the alcohol-containing wash buffer RPE (QIAGEN). The membrane was dried by a 2 min centrifugation at 14.000 rpm. Finally, the RNA was eluted twice by applying 40 µl of water to the membrane, followed by a 1-minute incubation and centrifugation for 1 min at 10.000 rpm.

Lysis Methods B, C and D

Lysis method B, C and D were performed as described above in Example 3, respectively.

As a control for each of the lysis methods the same lysis protocols were performed, however omitting the DNase pretreatment step according to the invention but using a state-of-the-art on-column DNase treatment instead. In other words, the addition of DNase pretreatment buffer and the DNase as well as the 15 min incubation at room temperature were omitted. Instead of the DNase pretreatment, the control samples were applied onto the silica membrane of an RNeasy column (QIAGEN), followed by a washing step with 350 µl of a chaotropic salt- and ethanol-containing washing buffer, such as RWT buffer (QIAGEN). Then, 80 µl of a mixture containing 70 µl of commercially available DNase-buffer RDD (QIAGEN) and 10 µl DNAse I (QIAGEN) were applied onto the silica membrane, followed by incubation for 15 min at room temperature. Following the on-column DNase treatment the control samples were washed once more with 350 µl of a chaotropic salt- and ethanol-containing washing buffer, such as RWT buffer (QIAGEN), followed by two washing steps with 500 µl of an alcohol-containing wash buffer, such as RPE (QIAGEN). The RNA was eluted as described above.

In order to determine efficiency of miRNA purification, the purified RNA was analyzed for detection and quantitation of miRNA 29a by real-time RT-PCR using the miScript PCR System (QIAGEN), according to the manufacturer's instructions. The mean values obtained from the ct values measured are shown in Table 6.

TABLE 6

|  | DNAse pretreatment | DNAse on-column treatment |
|---|---|---|
| lysis A | 26.9 | 31.2 |
| lysis B | 26.1 | 29.0 |
| lysis C | 26.0 | 31.7 |
| lysis D | 25.8 | 29.5 |

In all cases, the ct values measured are much lower in whole blood samples with DNAse pretreatment, whereas DNAse on-column treatment results in significant higher ct values. Lower ct values represent higher amounts of miRNA, in which a ct value difference of one is indicative of about the double amount of detected miRNA. The resulting ct-differences of up to and even over 5 show, that DNAse pretreatment enhances miRNA purification efficiency from whole blood samples significantly over the procedure according to the state-of-art.

Example 5: DNAse Treatment for Efficient miRNA Purification from Tissue Samples

For this experiment rat heart tissue was used. Immediately after resection, the tissue samples were stabilized in RNALater (QIAGEN), according to the manufacturer's instructions, and then stored at −80° C. until RNA isolation. In order to exclude experimental variations due to potential inherent differences in tissue samples, master lysates consistent of 100-130 mg rat heart starting material were prepared. For each 10 mg of tissue either 300 µl of a chaotropic agent containing buffer such as RLT (QIAGEN, lysis method A—see example 3), 300 µl of an aqueous lysis buffer containing a detergent such as PKD (QIAGEN, see lysis method D of example 3), or 700 µl of a phenol and chaotrop containing buffer such as QiaZol (QIAGEN, see lysis method B of example 3) were used (table 7):

TABLE 7

| lysis method | buffer type | tissue weight | Buffer volume |
|---|---|---|---|
| A | RLT(+β-Me) | 102 mg | 3060 µl |
| B | QIAZol | 130 mg | 9100 µl |
| D | PKD | 101 mg | 3030 µl |

Tissue samples were homogenized using the large rod in a rotor-statorhomogenizer like TissueRuptor (QIAGEN) for 30-60 sec in presence of the respective lysis buffer (50 ml falcon). To reduce the foaming during lysis method D and thus simplify the aliquotation process of the master lysates, the homogenates were left aside for 5-10 prior to aliquoting (300 µl aliquots for method A, 700 µl for method B and 290 µl for method D). Aliquots representing each 10 mg of tissue were used in duplicates with three different methods for purification of RNA including small RNAs (lysis method A, B and D) according to the present invention.

All three lysis protocols were described above in example 3, in which lysis method A correlates with method A, lysis method B with method B and method D with method D.

As a control for each of the lysis methods the same lysis protocols were used, however, the DNase pretreatment step according to the invention was omitted. Instead, a state-of-the-art on-column DNase treatment was performed to digest the DNA. In other words, the addition of DNase pretreatment buffer and the DNase as well as the 15 min incubation at room temperature were omitted. In place of the DNase pretreatment, the control samples were applied onto the silica membrane of a spin column such as RNeasy column (QIAGEN), followed by a washing step with 350 µl of a chaotropic salt- and ethanol-containing washing buffer, such as RWT buffer (QIAGEN). Then 80 µl of a mixture containing 70 µl of commercially available DNase-buffer RDD (QIAGEN) and 10 µl DNAse I (QIAGEN) were applied onto the silica membrane, followed by incubation for 15 min at room temperature.

Following the on-column DNase treatment the control samples were washed once more with 350 µl of a chaotropic salt- and ethanol-containing washing buffer, such as RWT buffer (QIAGEN), followed by two washing steps with 500 µl of an alcohol-containing wash buffer, such as RPE (QIAGEN). The RNA was eluted as described above.

In order to determine the efficiency of miRNA purification, the purified RNA was analyzed for detection and quantitation of miRNA 29a by real-time RT-PCR using the miScript PCR System (QIAGEN), according to the manufacturer's instructions. The mean values obtained from the ct values measured are shown in Table 8.

TABLE 8

|  | DNAse pretreatment | DNAse on column treatment |
|---|---|---|
| lysis A | 25.4 | 26.2 |
| lysis B | 23.5 | 25.0 |
| lysis D | 23.6 | 25.4 |

In all cases, the ct values measured are lower in tissue samples with DNAse pretreatment, whereas on-column DNAse treatment results in significant higher ct values. Lower ct values represent higher amounts of miRNA, in which a ct value difference of one is indicative of about the double amount of detected miRNA. Thus, DNAse pretreatment significantly enhances miRNA purification efficiency from tissue samples over the procedure according to the state-of-art.

The invention claimed is:

1. A method for isolating RNA from a RNA and DNA containing sample, said method comprising at least the following steps:
   a) degrading the sample;
   b) optionally separating undissolved constituents from the degraded sample;
   c) incubating at least a portion of the degraded, optionally further processed sample with a DNase, wherein the degraded, optionally further processed sample is not a nucleic acid sample that is bound to a solid phase, and wherein the degraded, optionally further processed sample is not a nucleic acid sample that has been eluted from a solid phase; and
   d) isolating RNA from the DNase treated sample.

2. The method according to claim 1, wherein said method is capable of isolating RNA including small RNA from said sample.

3. The method according to claim 1, wherein
   i) step a) is performed in the presence of at least one degrading additive selected from the group consisting of proteolytic enzymes, detergents, organic solvents, chaotropic agents and alkaline agents;
   ii) step a) is supported by mechanical degradation, homogenisation and/or heating; and/or
   iii) in step a), an aqueous solution comprising at least one degrading additive is added to the sample.

4. The method according to claim 1, wherein step c) is performed:
   i) in the absence of organic solvents in a concentration that inactivate the DNase;
   ii) in the absence of chaotropic agents in a concentration that inactivate the DNase;
   iii) in the presence of $Mg^{2+}$ and $Ca^{2+}$ in concentrations at which the DNase is active; and/or
   iv) in the presence of $Mg^{2+}$ and $Ca^{2+}$ in concentrations at which the DNase is active, wherein the $Mg^{2+}$ and the $Ca^{2+}$ are provided in the reaction composition in a concentration selected from the group consisting of at least 0.2 mM each, at least 2 mM each, at least 5 mM each, at least 7.5 mM each, at least 10 mM each or in a concentration range for each ion selected from the group consisting of 0.2 mM to 1 M, 2 mM to 100 mM, and 10 mM to 50 mM.

5. The method according to claim 1, wherein step d) comprises adding to the DNase digested sample additives appropriate for binding RNA to a nucleic acid-binding solid phase, and binding RNA in the DNase digested sample to the nucleic acid-binding solid phase.

6. The method according to claim 5, wherein the additives comprise at least one alcohol and/or at least one chaotropic agent, wherein step d) comprises at least the following steps:
   (1) adding the at least one alcohol and/or the at least one chaotropic agent and optionally further additives to the DNase treated sample to form a binding mixture and contacting the binding mixture with a nucleic acid-binding solid phase to bind the RNA to said solid phase;
   (2) optionally washing the RNA while it is bound to the solid phase; and
   (3) optionally eluting the RNA from the solid phase.

7. The method according to claim 5, wherein the nucleic acid-binding solid phase is comprised in a column or plate.

8. The method according to claim 1, wherein the RNA- and DNA-containing sample is selected from the group consisting of cells, clinical samples, body fluids, tissue, blood, blood products, plants, bacteria, viruses, fungi, human and animal sample material, environmental samples, lysates, RNA containing pellets obtained from a biological sample, fixed samples, cross-linked samples, FFPE samples and deparaffinized cross-linked samples.

9. The method according to claim 1, wherein the RNA- and DNA-containing sample is not a sample which is fixed by cross-linking.

10. The method according to claim 1, wherein the sample is fixed by cross-linking to form crosslinks some of which involve RNA, and
    wherein at least the cross-links that involve RNA are reversed prior to isolating the RNA.

11. The method according to claim 10, wherein step a) comprises partial degradation of the sample by partial proteolysis of the protein-containing components of the sample using at least one proteolytically active compound to selectively release the RNA into a dissolved fraction of the sample, while the DNA predominantly remains in the undissolved fraction of the sample, wherein the dissolved fraction comprises at least 50% RNA based on the total amount of nucleic acids in the dissolved fraction, and the undissolved fraction comprises at least 50% DNA based on the total amount of nucleic acids in the undissolved fraction.

12. The method according to claim 10, wherein
    i) step a) comprises adding an aqueous buffer solution to the sample;
    ii) in step a), a proteolytic enzyme is used for partial or complete proteolysis;
    and/or
    iii) step a) comprises heating the sample.

13. The method according to claim 11 comprising step b), wherein step b) comprises separating the dissolved fraction from the undissolved fraction.

14. The method of claim 13 wherein
    i) step b) is assisted by one or more techniques selected from the group consisting of sedimentation, filtration and centrifugation;
    ii) step b) is assisted by cooling the degraded sample either prior to or during separation; and/or
    iii) in step b), the undissolved fraction is obtained in form of a pellet.

15. The method according to claim 13, wherein the separated, dissolved fraction of the degraded sample is incubated with the DNase in step c).

16. The method according to claim 10, wherein the sample fixed by cross-linking is a paraffin-embedded sample.

17. The method of claim 16, wherein the method comprises prior to step a), step i) for the removal of the paraffin.

18. The method according to claim 10, wherein at least a portion of the cross-links in the sample is reversed by heating the degraded sample in the presence of a nucleophilic reagent.

19. The method according to claim 13, wherein
    a) the undissolved fraction is discarded; or
    b) the DNA is obtained from the undissolved fraction.

20. The method according to claim 13, further comprising obtaining the DNA from the undissolved fraction by:
    i) releasing the DNA from the undissolved fraction by subjecting said undissolved fraction to lysis with simultaneous enzymatic protease digestion, wherein the lysis is achieved by adding at least one detergent and optionally, further additives;

ii) heating the fraction from step i) to at least partially reverse the cross-links, and iii) isolating the DNA after reversing the cross-links, optionally by establishing binding conditions by adding appropriate additives and binding the DNA to a solid phase.

21. The method of claim 16, wherein the paraffin-embedded sample is a formalin-fixed paraffin-embedded sample (FFPE sample).

22. The method of claim 17, wherein step i) is performed by bringing the sample into contact with a hydrophobic organic solvent, optionally with addition of a $C_1$-$C_5$-alcohol.

23. The method of claim 22, wherein the hydrophobic organic solvent is an apolar aliphatic or aromatic hydrocarbon of a chain length of more than 6 and less than 17 carbon atoms or mixtures thereof.

24. The method of claim 22, wherein step i) is performed by bringing the sample into contact with a hydrocarbon or hydrocarbon mixture selected from the group consisting of xylene, heptane and mineral oil, optionally with addition of 1-25% by volume of methanol or ethanol.

* * * * *